United States Patent [19]

Mitchell

[11] Patent Number: 4,831,163

[45] Date of Patent: May 16, 1989

[54] IMPROVED METHOD FOR THE PREPARATION OF 1,4-CINEOLE

[75] Inventor: Peter W. D. Mitchell, Freehold, N.J.

[73] Assignee: Union Camp Corporation, Wayne, N.J.

[21] Appl. No.: 77,158

[22] Filed: Jul. 24, 1987

[51] Int. Cl.$^4$ ............................................. C07D 307/00
[52] U.S. Cl. ..................................... 549/463; 549/397
[58] Field of Search ................................ 549/397, 463

[56] References Cited

FOREIGN PATENT DOCUMENTS 345517 4/1930 United Kingdom ................ 549/397

*Primary Examiner*—Jane T. Fan
*Attorney, Agent, or Firm*—Edward J. Sites

[57] ABSTRACT

A method is provided for preparing cineole in an improved yield and with increased 1,4- isomer content, by reaction of terpin hydrate or terpineol with an acid, such as phosphoric acid, with distillation of the cineole from the reaction mixture as the cineole is formed.

15 Claims, No Drawings

IMPROVED METHOD FOR THE PREPARATION OF 1,4-CINEOLE

The invention relates to a method for the preparation of cineoles by the rearrangement of a terpin hydrate or terpineol.

BACKGROUND OF THE INVENTION

Cineoles are terpene ethers. Cineoles have been isolated from natural sources such as oils of wormwood and eucalyptus, or made synthetically from bicyclic terpene hydrocarbons, dipentenes, isoprenes, limonene, terpin hydrate, or terpineols. 1,4-Cineole (formula 1) is a by-product of the pine oil reaction

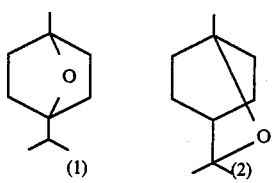

(the hydration of alpha-pinene under acid conditions). It occurs along with 1,8-cineole (formula 2) in about 6% of the crude product. The traditionally more desirable 1,8-cineole is also known as eucalyptol or 1,1,3-trimethyl-2-oxabicyclo[2.2.2] octane or 1,8-epoxy-p-menthane. The term cineole when used herein without numerical prefixes is inclusive of both the 1,4- and the 1,8-cineole isomers.

1,8-Cineole is a valuable aroma and pharmaceutical chemical, and much attention has been given to its synthesis, isolation, and purification. The technology of isolation of 1,8-cineole and one advantageous method for conducting this isolation is discussed in a recent patent of the present applicant, U.S. Pat. No. 4,521,608 (1985). Much less is known about preparation and isolation of 1,4-cineole, which at one time was viewed as the less valued isomer. The utility of 1,4-cineole as a synthetic intermediate has recently been recognized. For instance, it has recently been found to be a valuable intermediate for the preparation of herbicides.

If good yields could be attained, it would be particularly attractive from a cost and availability standpoint to make cineoles from pine oil which is available domestically in large quantities from the acid treatment of technical alpha-pinene. I have found that 1,4-cineole is less stable than 1,8-cineole under the acid conditions of the pine oil forming reaction but that, nevertheless, it is formed in equal or greater amounts than is 1,8-cineole. This finding indicated that there was the potential for achieving higher yields of 1,4-cineole if it could be removed from the reaction mixture as formed before any degradation could occur. It has been difficult to prepare cineole in good yield from pine oil by use of any known prior art methods, and it has been particularly difficult to prepare 1,4-cineole from that source. Fractional distillation to separate 1,4- from 1,8-cineole has been found quite difficult, if not commercially infeasible, unless means can be found for supplying a feed to the still having the 1,4- isomer substantially enriched relative to the 1,8- isomer.

The rearrangement of terpineols in the presence of mineral acid is a known procedure for making cineoles; see for example U.S. Pat. No. 1,994,131. It was shown to be necessary to control carefully the temperature, pressure, and acid concentration to avoid the undesired dehydration of the terpineol to an olefin. However, even with the selection of optimum rearrangement conditions, the yields of cineole from terpineols were quite low. In the prior art method of preparing alpha-terpineol, a solution of terpin hydrate in very dilute mineral acid or organic acid is steam distilled and the terpineol codistills with the water. However, if this essentially batchwise process is run with higher acid concentration, hydrocarbons become the major product, and little or no cineole is isolable.

The present invention is an improvement in the prior art method of preparing cineole, resulting in greater overall yields of cineole. The invention also makes possible the synthesis of the less-acid-stable isomer of cineole, namely 1,4-cineole, in much better yield than hitherto possible.

SUMMARY OF THE INVENTION

The invention comprises, in a method of preparing cineole which comprises rearranging a terpineol or partially dehydrating and rearranging terpin hydrate, the improvement which comprises carrying out said rearrangement of terpineol or partial dehydration and rearrangement of terpin hydrate, under conditions of continuous distillation of the cineole as it is formed.

The method of the invention provides improved yields of cineole product and, in particular, much improved yields of the less-acid-stable isomer 1,4-cineole.

Nowhere has it been taught or suggested in the prior art that the cineole products are capable of surviving in the reaction medium in which they are formed and thus that a great advantage would ensue if they were constantly removed as formed. Likewise, it has not been hitherto recognized that the 1,4- isomer of cineole in particular is especially transitory in the reaction mixture in which cineoles are formed and that constant removal by distillation as formed affords a means to make 1,4-cineole in greatly improved yields.

DETAILED DESCRIPTION OF THE PREFERRED EMBODIMENTS OF THE INVENTION

The method of the invention is carried out by the reaction of a terpene alcohol, selected from the group consisting of terpin hydrate and a terpineol, with a strong acid under distillation conditions in which the cineole is distilled out of the reaction mixture as it forms. A preferred mode of conducting this process is with 10–90% phosphoric acid, more preferably about 30% phosphoric acid, as the strong acid at a temperature of from 10°–110° C., more preferably at about 80° C., under vacuum.

Terpin hydrate is a saturated terpene diol which is produced, for example, from oil of turpentine. It is the cis-terpin hydrate of cis-terpin, or cis-p-menthane-1,8-diol. "Cis" refers to the relative positions of the 1-hydroxy and 4-hydroxy-propyl groups. Obviously, the anhydrous form could be used as well, but in the water-containing acid reaction medium it would presumably by hydrated. By the term terpineol is meant any of the monounsaturated terpene monohydric alcohols, including but not limited to alpha-terpineol, beta-terpineol, delta-terpineol, gamma-terpineol, terpinen-1-ol, terpinen-4-ol, p-menth-2-en-8-ol, p-metth-8-en-1-ol, p-menth-3-en-1-ol, p-menth-1(7)-en-4-ol, or mixtures thereof, such as occur in "produced pine oil" or "pine oil and heavier" technical products made by hydration of pinene using acid catalyst. It will be evident to one skilled in the art of terpene chemistry that acid catalyzed reactions of terpene alcohols are replete with double bond and hydroxy group rearrangements, and many isomers of the starting terpineol can yield the same final product. It will also be evident that the process of the invention may be run subsequently to the pinene hydration in the same vessel, and using either a fresh charge of acid or the acid left from the pinene hydration step, boosted if necessary to the higher concentration preferred for the cineole forming step.

One may surmise that under the conditions of the reaction to form cineole, terpin hydrate may undergo dehydration to form terpineoles, so that the cineole-forming process starting from terpin hydrate may proceed mainly or to a large degree by way of terpineols as intermediates, since it is known that terpin hydrate can react with acids to form terpineols (see for example, Bedoukian, "Perfume and Flavoring Synthesis," 2nd Edition, 1967, p. 340). However, we do not wish to be bound by this hypothesis, since the relative rates of the dehydration and the rearrangement steps are not known with any degree of certainty. The relative advantages of the use of terpin hydrate compared to the use of terpineols as starting materials will depend on cost and engineering considerations. Terpin hydrate is somewhat easier to isolate in good yield from pine oil. Terpin hydrate is also higher boiling than terpineols so that less of it will codistill with the cineole in the process of the invention. On the other hand, even if terpineols do codistill to some extent with the cineole, it is possible to recover and recycle the terpineols. It would entail an extra and unnecessary step to convert the terpineols back to terpin hydrate even if this were practicable, or alternatively, a complex flow sequence would be required with terpin hydrate being fed at one point and recycle terpineols being fed at another point. Moreover, since starting with terpineols results in no water formation in the cineole-forming reaction, the aqueous acid suffers less dilution. Thus, starting with terpineols permits use of lower acid strengths to begin with, and simplifies the recovery and recycle of the acid. Obviously, since either terpin hydrate or terpineol can be used in the process of the invention, a mixture of them can be used also.

We have found unexpectedly that by selection of certain terpineols or a feed rich in certain terpineols, the level of 1,4-cineole relative to 1,8-cineole can be raised, thus greatly simplifying the purification of the 1,4-cineole. In particular, by selection of terpinen-1-ol, terpinen-4-ol, or to a lesser extent beta-terpineol the yield of 1,4-cineole will be much higher than the yield of 1,8-cineole, up to 10 times as high. By contrast, using a typical alpha-terpineol as starting material, the ratio of 1,4- to 1,8-cineole may be in the vicinity of 1.9:1. the strong acid to be used in the process of the invention may be a mineral acid, such as sulfuric, phosphoric,, sulfamic, or a strong organic acid such as toluenesulfonic, xylenesulfonic, methylsulfonic, oxalic, formic, chloroacetic, or methyl phosphoric, to cite a few examples. Where a strong mineral acid is used, some water should be present. The preferred mineral acid is phosphoric acid in a concentration range of 10 to 90% and most preferably about 30%. The mole ratio of acid to terpene alcohol should be in the range of 10:1 to 1:10. Where terpin hydrate is used as the terpene alcohol reactant, about 2 moles acid to 1 mole of terpin hydrate is preferred. Phosphoric acid in the vicinity of 30% concentration is most preferred because of maximum yields (in the range of 25-30% of 1,4-cineole) obtained with its use when the reaction temperature is in the vicinity of about 80° C.. When more dilute acid is used, more terpineol is found in the distillate; when more concentrated acid is used, more hydrocarbons are formed.

The distillation conditions to be used in the process of the invention are those that permit cineole to be distilled out at temperatures at which it is stable long enough to escape the reaction mixture. Thus, vacuum distillation conditions are greatly preferred although with a short path still arrangement, such as a wiped film or falling film still, atmospheric pressure may be usable. It is however, preferred to use vacuum even if such short path distillation apparatus is employed. The vacuum should be such that cineole distills out at the chosen reaction temperature; typical vacuums may be in the range of 200 to 450 mm, as an example.

The distillation apparatus used may be a simple still or reactor operable as a still without a fractionating column or it can have a fractionating column, although it is not desirable to impose a long delay on the disengagement of the cineole from the reactor. Thus, if a column is used, it should not have a long hold up nor be operated at a high reflux ratio. Preferably, no reflux of cineole-containing product to the reactor should occur.

The reactor is preferably operated in a continuous mode in respect to the disengagement of cineole, although it will be recognized that a periodically repeated batch distillation of cineole product, before much accumulates in the reactor, can approximate continuous distillation. It is less important that the terpin hydrate or terpineol feed to the reactor be continuous although there is some advantage. The main requirement is that the cineole be removed quickly after it is formed in order to obtain good cineole yields. Physical means to improve the disengagement of vapors is advantageous but not necessary. Such physical means include sparging, agitation, and use of falling film or wiped film technique as are well known in the art of distillation. The so-called molecular still or short path still design is well suited. Any means which minimizes the residence of cineole in the reaction zone is advantageous. The improved method of the invention may be carried out in the presence of an inert solvent for the starting terpene alcohol if a solvent is used which either codistills or boils higher than cineole. The solvent can act as a "chaser" to aid the complete distillation of the cineole. The term "inert solvent" means one which does not enter into or adversely affect the desired reaction.

Representative solvents with boiling points in the approximate range of cineole (176° C.) and which will codistill with cineole include but are not limited to aliphatic hydrocarbons such as decanes; aromatic hydrocarbons such as cumene or pseudocumene; halogenated hydrocarbons such as orthodichlorobenzene; ethers such as phenetole; or esters such as methyl benzoate. Solvents boiling above cineoles and which have the advantage of permitting easier separation are exemplified by dodecane and higher alkanes; methylnaphthalenes and other heavy aromatic naphthas boiling above cineole; trichlorobenzene; diphenyl ether; higher benzoates; and in general any chemically inert solvent boiling above cineoles.

The reaction temperature may be from 10° C. to 120° C., preferably from 30° to 110° C.. With the preferred phosphoric acid of concentration in the range of 10 to 90%, the reaction temperature is preferably in the range of 60° to 110° C. With the most preferred phosphoric acid of about 30% concentration, a reaction temperature of about 80° C. is optimum. The amount of acid is not set by stoichiometry since it is not used up, but empirically a ratio of about 2 moles of acid per mole of terpene alcohol is found preferably when terpin hydrate is used as the terpene alcohol starting material.

The process of the invention can be run in a vessel fitted to serve as both reactor and still. It is preferably stirred and the feed, terpin hydrate or terpineol, is introduced either continuously or batchwise, with continuous distillation of cineole as soon as any substantial amount of cineole has formed.

The process of the invention can be conveniently run as a continuous step following the usual process for pinene hydration to terpin hydrate. The pinene hydration can be run in the known manner using phosphoric acid and the reaction mixture then pumped into a second reactor in which the acid concentration is adjusted into the cineole-forming range and the cineole product continuously distilled from this reactor as it forms; alternatively the two steps can be run in a single reactor, the concentration of acid being adjusted to the cineole-forming range after the pinene hydration step is completed, and the distillation of the cineole then commenced.

The product at the end of the reaction is recovered as the condensed distillate from the reaction. If a solvent has been used and has codistilled, the cineole may conveniently be separated from the solvent by redistillation, which at this stage can entail a slower and more precise fractionation because the cineole has now been removed from the deleterious effects of the acid. Any unreacted terpene alcohols which may have codistilled with the cineole can be removed at this step for possible recycle, and any terpene hydrocarbons which may have codistilled with the cineole can be removed at this step for possible recycle, and any terpene hydrocarbons which may have codistilled can also be removed from the product at this step. It is even possible to separate the cineole isomers by fractional distillation at this point, although they are very close boiling. Various other methods, including those in the prior art, can be used to separate 1,4- and 1,8-cineole. These include selective complexation with hydroquinone or with zeolites. Various methods are reviewed by Goldstein in U.S. Pat. No. 4,347,189 (1982), col. 2.

The following examples describe the manner and process of the invention and set forth the best mode contemplated by the inventors for carrying out the invention but are not to be construed as limiting.

EXAMPLE 1

A reactor fitted with a stillhead, condenser, and receiver for distillate and connected to a vacuum line so that a vacuum could be established in the reactor. Into this reactor was placed 30 g. terpin hydrate, 50 mls. 30% phosphoric acid, and the mixture was heated to a pot temperature of 80° C. while a vacuum of 328 mm of mercury was applied. Over a period of min., a distillate was collected in three portions, and analyzed by gas chromatography (gc), with results as shown in the following table:

| Fraction | 1 | 2 | 3 |
|---|---|---|---|
| Wt. (g.) | 8.5 | 7.1 | 7.6 |
| Component %: | | | |
| 1,4-cineole | 29.73 | 25.89 | 24.23 |
| a-terpinene | 5.34 | 8.50 | 9.10 |
| limonene | 14.78 | 11.41 | 7.35 |
| 1,8-cineole | 15.69 | 14.56 | 11.82 |
| g-terpinene | 3.75 | 7.30 | 11.67 |
| terpinolene | 18.90 | 20.52 | 23.76 |
| Total 1,4-cineole: 6.21 g. equivalent to 25.5 mole % yield. | | | |
| Total 1,8-cineole: 3.25 g. equivalent to 13.4 mole % yield. | | | |

EXAMPLE 2

In a similar apparatus and manner, 20 g. terpin hydrate, 20 g. oxalic acid and 100 g. water were reacted at the boiling point (slightly above 100° C.) while taking off water (total 18.18 g.) and organic distillate (total 12.95 g.) continuously through a Vigreux column. The organic distillate was found by gc to contain 15.82% 1,4-cineole and 14.93% 1,8-cineole.

EXAMPLE 3

In a similar manner to example 1, 30 g. of terpin hydrate was reacted with 50 ml. of 30% phosphoric acid with continuous removal of the distillate. Various distillation columns and distillation conditions were tried with results as shown in the following table:

| Distillation Column | Temp. (C.°) | Acid Conc. (wt. %) | 1,4-cineole Yield (%) |
|---|---|---|---|
| none | 80 | 30 | 23.6 |
| packed | 80 | 30 | 22.7 |
| Vigreux | 80 | 30 | 22.4 |
| none | 85 | 40 | 21.8 |
| Vigreux | 80 | 40 | 19.9 |
| Vigreux | 88 | 30 | 16.7 |
| Oldershaw | 88 | 30 | 16.7 |
| Vigreux | 88 | 50 | 15.8 |
| none | 100 | 20 | 15.4 |
| Oldershaw | 88 | 50 | 14.8 |
| Oldershaw | 88 | 40 | 14.1 |
| Vigreux | 80 | 60 | 11.7 |
| Vigreux | 80 | 50 | 8.6 |
| Vigreux | 88 | 60 | 8.3 |
| Oldershaw | 88 | 60 | 7.4 |
| Oldershaw | 88 | 70 | 7.2 |
| none | 85 | 20 | 7.1 |
| Vigreux | 105 | 70 | 6.7 |

Some advantage is noted in the use of no column which facilitates rapid removal of the cineole as it is formed. The best results are noted at 80° C. and with 30% phosphoric acid.

EXAMPLE 4

A mixture of 240 g. alpha-terpineol (82%) and 1000 g. of 30% phosphoric acid was charged to a reactor fitted with a 10-plate Oldershaw distillation column. The organics were distilled at 80° C. and 290 mm Hg. A typical distillate sample, contained 25.3% 1,4-cineole and 11.0% 1,8-cineole.

What is claimed is:

1. In a method for preparing cineole by reacting a terpene alcohol with a strong acid, the improvement which comprises preferentially preparing 1,4-cineole by reacting a terpene alcohol selected from the group consisting terpene hydrates and terpineols with phosphoric acid at a temperature from 80° to 100° C. to form 1,4- cineole and 1,8-cineole and then removing the 1,4-cineole and 1,8-cineole from the reaction mixture as quickly as they are formed in the reaction mixture to produce a reaction mixture having an increased yield of 1,4-cineole as compared to 1,8-cineole.

2. The method of claim 1, wherein the terpineol is a mono-unsaturated terpene monohydric alcohol.

3. The method of claim 2, wherein the terpineol is terpinen-1-ol, terpinen-4-ol, or beta-terpineol.

4. The method of claim 1, wherein the mole ratio of phosphoric acid to terpene alcohol is in the range of from about 10:1 to 1:10.

5. The method of claim 1, wherein the phosphoric acid is in a concentration of about 30% by weight.

6. The method of claim 1, wherein the terpene alcohol is terpin hydrate and the terpin hydrate is present in a ratio of from about 2 moles of phosphoric acid to 1 mole of terpin hydrate.

7. The method of claim 1, wherein the reaction temperature is 80° C.

8. The method of claim 1, wherein the 1,4-cineole and 1,8-cineole are removed from the reaction mixture by distillation selected from the group of sparging, agitation, falling film technique, or wiped film technique.

9. The method of claim 1, wherein the reaction is carried out in the presence of an inert solvent having a boiling point equal to or greater than 1,4-cineole and 1,8-cineole.

10. The method of claim 9, wherein the inert solvent is an aliphatic hydrocarbon, an aromatic hydrocarbon, a halogenated hydrocarbon, an ether, or an ester.

11. The method of claim 10, wherein the inert solvent is selected from the group consisting of decanes, cumene, pseudocumene, orthodichlorobenzene, phenetole, and methyl benzoate.

12. The method of claim 9, wherein the inert solvent is dodecane or a higher alkane, methylnaphthalene, trichlorobenzene, or diphenyl ether or a higher benzoate.

13. The method of claim 1, wherein the procedure is continuous.

14. The method of claim 1, wherein the procedure is batchwise.

15. The method of claim 1, wherein in an additional step the 1,4-cineole is separate from the 1,8-cineole.

* * * * *